United States Patent
Rossman et al.

(10) Patent No.: US 10,137,227 B2
(45) Date of Patent: *Nov. 27, 2018

(54) BONE MARROW ASPIRATION DEVICE

(71) Applicant: SpineSmith Partners, L.P., Austin, TX (US)

(72) Inventors: John B. Rossman, Austin, TX (US); Richard J. Kana, Lexington, TX (US)

(73) Assignee: SpineSmith Partners, L.P., Austin, TX (US)

( * ) Notice: Subject to any disclaimer, the term of this patent is extended or adjusted under 35 U.S.C. 154(b) by 513 days.

This patent is subject to a terminal disclaimer.

(21) Appl. No.: 14/642,295

(22) Filed: Mar. 9, 2015

(65) Prior Publication Data

US 2015/0250929 A1 Sep. 10, 2015

Related U.S. Application Data

(60) Provisional application No. 61/950,140, filed on Mar. 9, 2014.

(51) Int. Cl.
*A61M 1/00* (2006.01)
*A61B 10/02* (2006.01)
*A61M 1/02* (2006.01)

(52) U.S. Cl.
CPC ........... *A61M 1/007* (2014.02); *A61B 10/025* (2013.01); *A61M 1/02* (2013.01); *A61B 2010/0258* (2013.01); *A61M 2202/10* (2013.01); *A61M 2205/0238* (2013.01)

(58) Field of Classification Search
CPC ................ A61M 1/02; A61M 2202/10; A61M 2205/0238; A61M 1/0068; A61B 10/025; A61B 2010/0258; A61B 10/0283; A61B 2010/0208; A61B 10/02; A61B 2010/0225; A61B 10/0266; A61B 17/3472; A61B 17/34; A61B 2217/005

See application file for complete search history.

(56) References Cited

U.S. PATENT DOCUMENTS

| | | | | |
|---|---|---|---|---|
| 5,318,782 A * | 6/1994 | Weis-Fogh | ............. | A61B 5/411 424/529 |
| 2003/0208181 A1* | 11/2003 | Geise | .................. | A61M 1/0218 604/406 |
| 2011/0082425 A1* | 4/2011 | Wuestemann | ....... | A61B 10/025 604/151 |
| 2014/0114285 A1* | 4/2014 | Gao | ...................... | A61M 5/204 604/522 |
| 2016/0354595 A1* | 12/2016 | Gallagher | .......... | A61B 10/0283 |

* cited by examiner

*Primary Examiner* — Tatyana Zalukaeva
*Assistant Examiner* — Gabriella Burnette
(74) *Attorney, Agent, or Firm* — Winstead PC

(57) ABSTRACT

An embodiment of the invention is directed to a bone marrow aspiration device comprising a plurality of syringes, each of which operates in a series of sequential steps to obtain bone marrow of high quality and therapeutic value, i.e., having a high mesenchymal stem cell ("MSC") MSC/ml number. In certain embodiments, a syringe may be used along with a collection vessel or with a second syringe. A further embodiment of the invention is directed to a method for using the bone marrow aspiration device as set forth herein.

7 Claims, 4 Drawing Sheets

BONE MARROW ASPIRATION DEVICE

CROSS-REFERENCES TO RELATED APPLICATIONS

This Application claims the benefit under 35 U.S.C. § 119(e) of U.S. Provisional Patent Application No. 61/950,140 filed Mar. 9, 2014 which is incorporated herein by reference in its entirety as if fully set forth herein.

BACKGROUND OF THE INVENTION

During bone marrow aspiration, a needle is injected into the cancellous bone. A syringe is connected to the needle to aspirate the bone marrow. It is known that the first rapid forceful pull of the syringe plunger is essential to the quality of bone marrow aspirate. However, different operators may apply different pulling force to the plunger and therefore inconsistent bone marrow aspiration is a concern. Aspirating bone marrow from the iliac crest using small volumes of 1-4 ml has been historically proposed for harvesting adult mesenchymal stem cells and described as a standard technique to avoid blood dilution. Studies have shown that bone marrow aspiration using a larger volume syringe (50 ml) as compared with a smaller volume syringe (10 ml) results in a reduced mesenchymal stem cell count in bone marrow aspirates. Recent studies have demonstrated that mesenchymal stem cells are pericytes, i.e., cells that have attachment to the vasculature. In order to release these cells repeated rapid application of pressure is required as opposed to steady pressure. The current invention provides an apparatus that applies a rapid pulling force to the plunger, reducing user variances while also allowing for a more consistent quality of aspirated bone marrow by maximizing mesenchymal stem cell content.

SUMMARY OF THE INVENTION

An embodiment of the invention is directed to a bone marrow aspiration device comprising a plurality of syringes, each of which operates in a series of sequential steps to obtain bone marrow of high quality and therapeutic value, i.e., having a high MSC/ml number. In certain embodiments, a single syringe may be used along with a collection vessel or a containment chamber. In other embodiments the containment chamber is replaced by a secon syringe. Another embodiment of the invention is directed to a method for using the bone marrow aspiration device as set forth herein.

DETAILED DESCRIPTION OF EXEMPLARY EMBODIMENTS

Figure 1A:
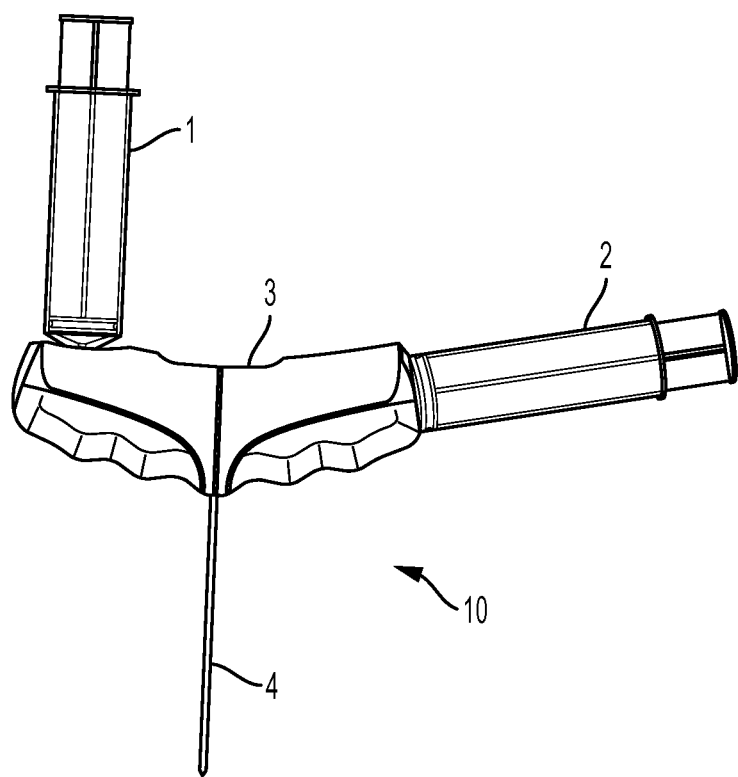
FIGS. 1A to 1D represent a bone marrow aspiration device in accordance with embodiments of the invention.

The advantages of the claimed invention include: streamlining bone marrow collection by reducing user variances; providing a rapid pull to improve the bone marrow aspirate quality and stem cell content; and assisting the operator for multiple bone marrow collections.

An embodiment of the invention is an apparatus that is designed to assist the operator in aspirating bone marrow. The apparatus comprises a housing and a plurality of syringes in certain embodiments. In other embodiments, the apparatus comprises a housing with a single syringe and a containment chamber. The apparatus also includes at least one needle which is designed to be placed in a bone marrow reservoir.

The apparatus employs at least one "trigger" mechanism that allows the user to control when aspiration begins. In certain embodiments, the design includes multiple triggers at different positions that allow for various forces and speeds of aspiration, depending on the user's preference.

The viscosity of bone marrow is 37.5-400 cPs. Using a 10 cc syringe at 30° C., the bone marrow flow rate is approximately 3-5 cc/sec when pulling the syringe plunger with a force of 60 N (Newtons). The ideal bone marrow flow rate during bone marrow collection (a rapid pull) is 5-10 cc/sec. One key metric for assessing the quality of a bone marrow aspirate sample is the "mesenchymal stem cell per milliliter" or "MSC/mL". Studies have shown that aspiration of a smaller volume of bone marrow than the total volume of a syringe pulled, results in higher MSC/mL. For example, experiments conducted on a test group of normal adults showed that the maximum MSC number (mean 2,062±1552) was obtained with an aspiration of 1 ml with a 10-ml syringe and the minimum MSC number (mean 95±8) was obtained with an aspiration of 50 ml with a 50-ml syringe. Additionally, the ease of drawing a small syringe allows greater application of force during aspiration. Both of these factors point to the preferred use of a syringe with a smaller volume than a syringe with a larger volume. Furthermore, studies have shown that repeated application of vacuum prevents in-flow of peripheral blood which has virtually no MSCs, into the aspirate. Thus, instead of a single aspiration site with a single syringe of large volume, a plurality of aspiration sites with repeated aspirations is recommended. The experiment also conclude that aspiration of only 10% of the full syringe volume resulted in a greater MSC concentration compared to syringes filled with progressively higher percentages of the full volume for either syringe size.

An embodiment of the invention is directed to a bone marrow aspiration device comprising a plurality of syringes, each of which operates in a series of sequential steps to obtain bone marrow of high quality and therapeutic value, i.e., having a high MSC/ml number. An embodiment of the invention preferably comprises two syringes, wherein a first syringe is used to aspirate bone marrow from a subject, which is exported into a second syringe that contains an anticoagulant. In other embodiments of the invention, the bone marrow is drawn into a syringe and exported into a tubing and into a collection vessel.

In an embodiment of the invention, one or more of the syringes of the device are connected to one another by tubing. The tubing that connects the syringes of the device is coupled to one or more valves that regulate the directionality of flow of fluids through the tubing and/or the syringes. In an embodiment of the invention, the syringe that is used to aspirate bone marrow from a subject (aspiration syringe) is connected to a needle having fenestrations at its tip.

In certain embodiments, the tubing and two valves are repalced by a directional valve that accomplishes the same function.

Needle characteristics include the ability to be hammered into the vertebral body or drilled; ergonomic shaping for easy handling; fenestrated but not cannulated through;

allows for draw in localized areas and prevents in flow of large amounts of peripheral blood; prevents needle from being clogged with bone and minimizes damage to iliac cortical bone; and is disposable one time use at the same cost of current "Jamshidi®" bone marrow biopsy needles.

In another embodiment of the invention, a tubing connects a syringe to a collection vessel and this tubing is coupled to one or more valves that regulate the directionality of flow of fluids through the tubing.

An embodiment of the invention is directed to a method for aspirating bone marrow from a subject comprising the steps of aspirating the bone marrow from a subject, mixing the bone marrow with an anticoagulant and mixing the bone marrow and anticoagulant in a reservoir for further storage.

An embodiment of the invention is a bone marrow aspiration device containing a plurality of syringes. One syringe is operated manually by the user, while the other is passively filled as the user operates the device. The sequential steps are intended to obtain bone marrow of high quality and therapeutic value that is they have a relatively high count of MSC's as compared to traditional aspiration techniques. An embodiment of the invention preferably comprises two syringes wherein the first syringe is used to aspirate bone marrow, and the second syringe is intended as a collection syringe as repeated draws are performed. The second syringe is coated with an anti-coagulant to prevent clotting in the aspiration sample. An embodiment of the device also has a needle that is placed into the body into a site rich in bone marrow which is to be harvested. An embodiment of the device also preferably has two one way valves which allow marrow to be aspirated into the syringe drawn back by the user through the needle but not pushed back into the needle. The second valve allows marrow to be passed into the collection syringe but not back into the device.

Another embodiment of the invention is a bone marrow aspiration device containing one syringe, a needle, and a containment chamber within the housing. In this embodiment the containment chamber takes the place of the secondary syringe. The entire device may then be used to evacuate the containment chamber.

An embodiment of the invention is directed to a device for extracting bone marrow from a subject comprising: a first syringe, a second syringe, a needle, two valves and a housing for the assembly; the first syringe is connected to a needle via tubing and a one-way valve which directs flow solely towards the first syringe; the first syringe is connected to a second syringe via tubing and a one way valve allowing flow solely from the first syringe into the second syringe.

A further embodiment of the claimed invention is directed to a method for extracting bone marrow from a subject comprising the steps of: providing a bone marrow aspiration device comprising a syringe attached to a needle; inserting the needle into a bone of a subject; creating a vacuum in the syringe sufficient to withdraw bone marrow from the subject through the needle into the syringe; filling a portion of the volume of the syringe with bone marrow; releasing the bone marrow from the syringe into a tubing by exerting pressure on the plunger of the syringe; and filling a containment chamber or second syringe with the released bone marrow from the first syringe.

In an embodiment of the invention the syringes and needle are connected by tubing. The tubing that connects the syringes and needle are coupled to one or more valves that regulate the directionality of the flow of fluids through the tubing and or the syringes. The tubing is also directly connected to a needle. All tubing and syringe connections are contained within a housing that may be used to apply pressure to insert the Jamshidi® bone marrow biopsy needle.

In an embodiment of the invention the first syringe is controlled manually. The syringe may be moved multiple times to collect as much marrow as is desired by the user.

In an embodiment of the invention a trumpet valve may be used to hold pressure between the needle in the first syringe. This allows the syringe to be drawn and held. When the trumpet valve is released the pressure may be immediately applied through the needle by opening or pressing the trumpet valve.

FIG. 1A depicts an aspect of the aspiration device 10. The device 10 has a housing 3 and two syringes that are connected to the housing. A first syringe or vacuum syringe 1 is connected to the housing 3 at a proximal location to the user. A second syringe or collection syringe 2 is connected to the housing 3 at a distal location to the user. A needle 4 is connected to the housing and is inserted into the region of the bone containing bone marrow for aspiration of the marrow.

Figure 1C:
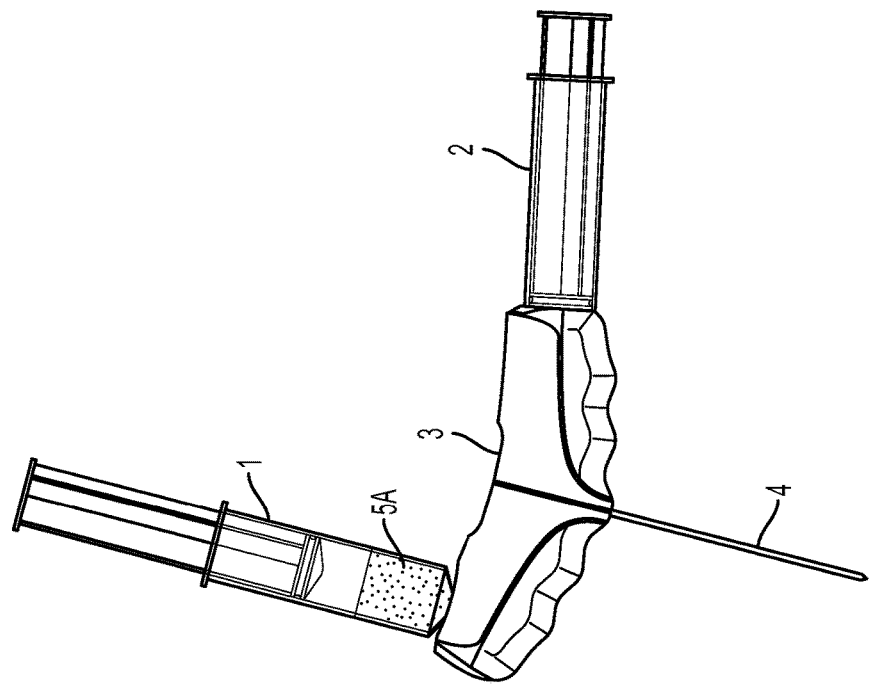
Figure 1B:
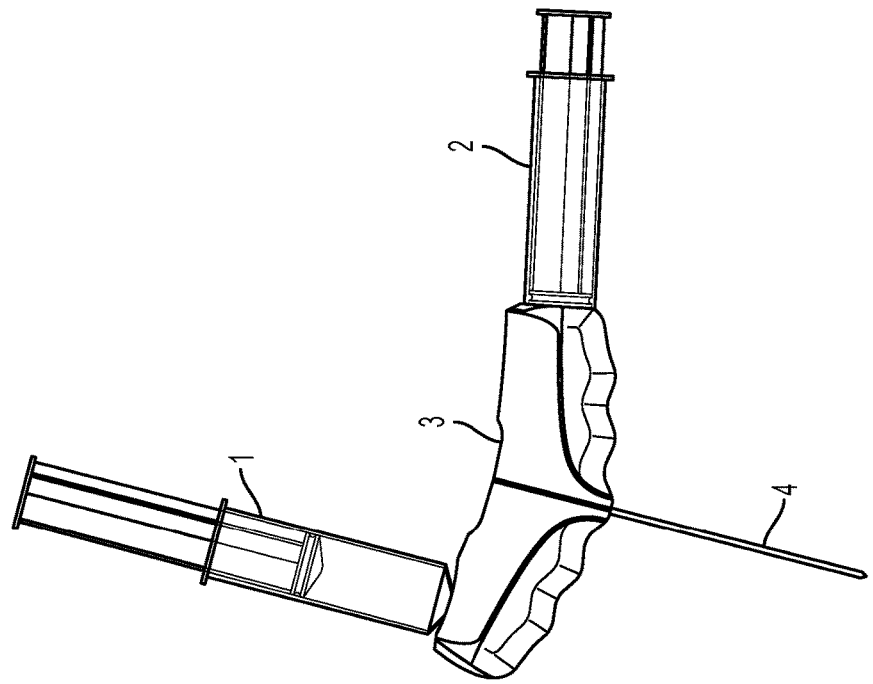

FIG. 1B shows the vacuum syringe 1 with its plunger drawn back to a fixed position and locked, while the plunger in the collection syringe 2 remains entirely within the barrel.

FIG. 1C shows the vacuum syringe 1 filled with bone marrow 5A to approximately half the available volume. After the syringe is filled with bone marrow to approximately half the available volume, the vacuum is released.

Figure 1D:
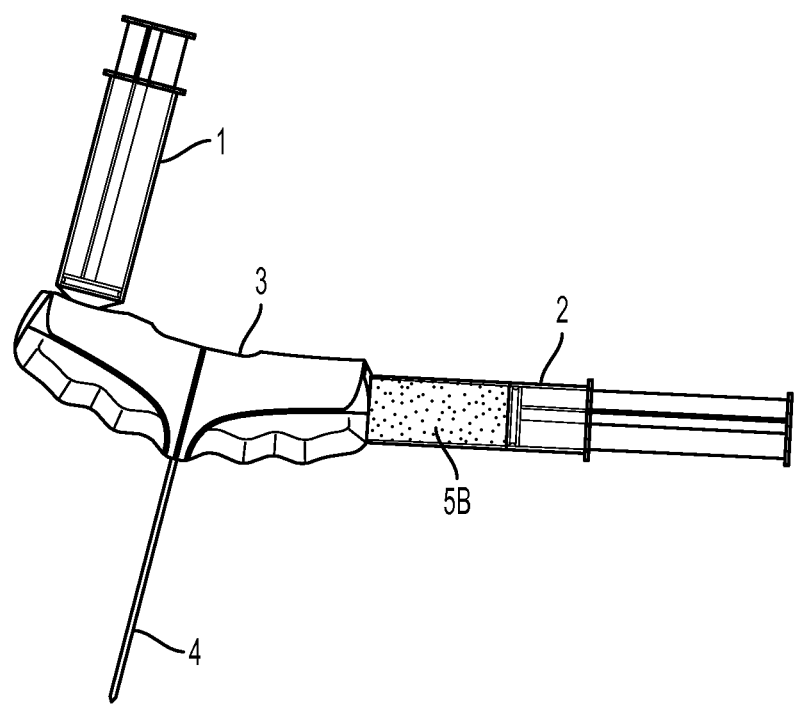
Figure 2:
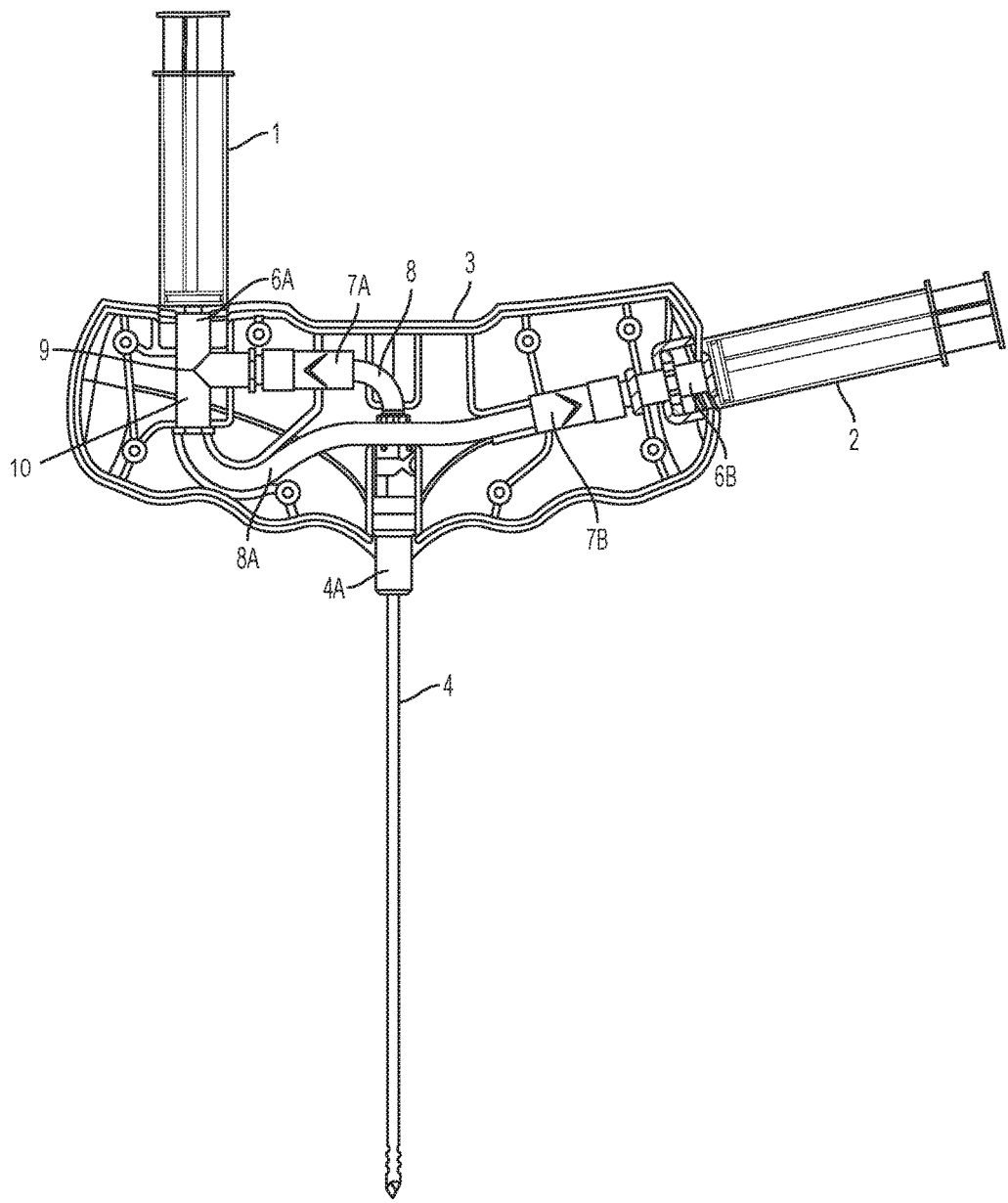
FIG. 2 represents a cross-sectional view of a bone marrow aspiration device in accordance with an embodiment of the invention.

FIG. 1D shows the plunger of the vacuum syringe 1 returned to its original position and bone marrow 5B is shunted to the collection syringe 2 through a one-way valve 7B (see FIG. 2).

FIG. 2 shows a cross-sectional view of the bone marrow aspiration device 10. Valve 7A directs flow of the bone marrow via tubing 8 exclusively to the vacuum syringe which is connected to the housing 3 at attachment point 6A. Valve 7B directs flow of the bone marrow exclusively to the collection syringe which is connected to the housing 3 at attachment point 6B. The valves are connected by a tubing 8A through which the marrow flows from the vacuum syringe 1 to the collection syringe 2 (or a containment chamber (not shown)). In certain embodiments of the invention, a trigger mechanism may be connected to the housing at position 9. As shown in FIG. 2, a coupler 10 connects flow paths of the vacuum syringe 1, the valve 7A, and the valve 7B. The needle 4 is connected to the housing 3 via a hub 4A. In certain embodiments, the needle 4 and hub 4A along with the tubing 8 are integral and permanently connected to the housing 3. In other embodiments, the needle 4 and hub 4A along with the tubing 8 are detachable from the housing 3.

In the preceding detailed description, the invention is described with reference to specific exemplary embodiments thereof and locations of use within the hip. Various modifications and changes may be made thereto without departing from the broader spirit and scope of the invention as set forth in the claims.

The invention claimed is:

1. A bone marrow aspiration device comprising:
   a housing configured to couple to a first syringe, a second syringe, and a needle;
   a first one-way valve disposed within the housing and positioned between the needle and the first syringe, the first one-way valve configured to allow a fluid to only flow from the needle to the first syringe;
   a second one-way valve disposed within the housing and positioned between the first syringe and the second syringe, the second one-way valve configured to allow a fluid to flow only from the first syringe to the second syringe; and a T-shaped coupler disposed within the housing and joining flow paths of the first syringe, the first one-way valve, and the second one-way valve together.

2. The device of claim 1, further comprising a tubing that connects the coupler to the second syringe.

3. The device of claim 1, wherein the needle is connected to the first syringe via a needle hub.

4. The device of claim 1, wherein the needle and first tubing are permanently connected to the housing.

5. The device of claim 1, wherein the needle is detachable from the housing.

6. A method for extracting bone marrow from a subject comprising the steps of:

inserting a needle of a bone marrow aspiration device into a bone of a subject, the bone marrow aspiration device comprising:

a housing configured to couple to a first syringe, a second syringe, and a needle;

a first one-way valve disposed within the housing and positioned between the needle and the first syringe, the first one-way valve configured to allow a fluid to only flow from the needle to the first syringe;

a second one-way valve disposed within the housing and positioned between the first syringe and the second syringe, the second one-way valve configured to allow a fluid to flow only from the first syringe to the second syringe; and a coupler disposed within the housing and joining flow paths of the first syringe, the first one-way valve, and the second one-way valve together;

creating a vacuum in the first syringe sufficient to withdraw bone marrow from the subject through the needle into the first syringe;

filling a portion of the volume of the first syringe with bone marrow;

releasing the bone marrow from the first syringe into the second tubing; and causing the second syringe to fill with bone marrow from the first syringe.

7. The method of claim 6, further comprising coating the second syringe with an anticoagulant.

\* \* \* \* \*